US011020193B2

(12) United States Patent
Wixey et al.

(10) Patent No.: US 11,020,193 B2
(45) Date of Patent: Jun. 1, 2021

(54) MEDICAL DEVICE DRIVE SYSTEM

(71) Applicant: Intuitive Surgical Operations, Inc., Sunnyvale, CA (US)

(72) Inventors: Matthew A. Wixey, San Jose, CA (US); Nicholas H. Ragosta, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 158 days.

(21) Appl. No.: 16/333,926

(22) PCT Filed: Sep. 8, 2017

(86) PCT No.: PCT/US2017/050731
§ 371 (c)(1),
(2) Date: Mar. 15, 2019

(87) PCT Pub. No.: WO2018/052810
PCT Pub. Date: Mar. 22, 2018

(65) Prior Publication Data
US 2019/0201148 A1     Jul. 4, 2019

Related U.S. Application Data

(60) Provisional application No. 62/395,364, filed on Sep. 15, 2016.

(51) Int. Cl.
*A61B 34/30* (2016.01)
*A61B 34/00* (2016.01)
(Continued)

(52) U.S. Cl.
CPC ............. *A61B 34/37* (2016.02); *A61B 34/00* (2016.02); *A61B 34/30* (2016.02); *A61B 90/03* (2016.02);
(Continued)

(58) Field of Classification Search
CPC ............ A61B 17/29; A61B 2017/2912; A61B 2017/2913; A61B 2017/2914;
(Continued)

(56) References Cited

U.S. PATENT DOCUMENTS 4,207,898 A    6/1980  Becht
5,312,023 A    5/1994  Green et al.
(Continued)

FOREIGN PATENT DOCUMENTS

WO    WO-2013084221 A1    6/2013
WO    WO-2015153636 A1    10/2015
WO    WO-2015175200 A1    11/2015

OTHER PUBLICATIONS

International Search Report and Written Opinion for Application No. PCT/US2017/050710, dated Dec. 14, 2017, 12 pages.
(Continued)

Primary Examiner — Shaun L David
Assistant Examiner — Joshua T Hicks
(74) Attorney, Agent, or Firm — Schwegman Lundberg & Woessner, P.A.

(57) ABSTRACT

A medical device system can include a surgical tool, and a one-way input, and a drive system operatively coupled to the surgical tool and the oneway input device. The drive system can be rotatable in a first direction to effectuate a first operation of the surgical tool, and rotatable in a second direction to effectuate a second the operation of the surgical tool. The one-way input device can be operable to rotate the rotatable drive system in the second direction but not the first direction.

8 Claims, 11 Drawing Sheets

(51) Int. Cl.
*A61B 90/00* (2016.01)
*A61B 17/00* (2006.01)
*A61B 34/37* (2016.01)

(52) U.S. Cl.
CPC .............. *A61B 2017/00407* (2013.01); *A61B 2017/00477* (2013.01); *A61B 2090/034* (2016.02)

(58) Field of Classification Search
CPC .... A61B 2017/2915; A61B 2017/2916; A61B 2017/2917; A61B 17/295; A61B 17/068; A61B 17/072; A61B 17/115; A61B 17/32057; A61B 17/3205; A61B 34/35; A61B 34/70; A61B 34/71
See application file for complete search history.

(56) References Cited

U.S. PATENT DOCUMENTS

| | | |
|---|---|---|
| 5,382,885 A | 1/1995 | Salcudean et al. |
| 5,609,601 A | 3/1997 | Kolesa et al. |
| 5,779,130 A | 7/1998 | Alesi et al. |
| 5,954,259 A | 9/1999 | Viola et al. |
| 6,770,081 B1 | 8/2004 | Cooper et al. |
| 7,485,127 B2 | 2/2009 | Nistal |
| 7,543,516 B2 | 6/2009 | Siefert |
| 7,780,651 B2 | 8/2010 | Madhani et al. |
| 7,802,664 B2 | 9/2010 | Hanna et al. |
| 7,918,230 B2 | 4/2011 | Whitman et al. |
| 7,984,663 B2 | 7/2011 | Dent |
| 8,640,921 B2 | 2/2014 | Meron et al. |
| 8,644,988 B2 | 2/2014 | Prisco et al. |
| 8,968,312 B2 | 3/2015 | Marczyk et al. |
| 9,060,860 B2 | 6/2015 | Morris et al. |
| 9,549,818 B2 | 1/2017 | Morrissey |
| 9,919,724 B2 | 3/2018 | Lubischer et al. |
| 1,059,103 A1 | 3/2020 | Wixey |
| 2003/0130677 A1 | 7/2003 | Whitman et al. |
| 2003/0216667 A1 | 11/2003 | Viola |
| 2007/0023477 A1 | 2/2007 | Whitman et al. |
| 2007/0270790 A1 | 11/2007 | Smith et al. |
| 2008/0177283 A1 | 7/2008 | Lee et al. |
| 2008/0245842 A1 | 10/2008 | Marczyk |
| 2008/0251568 A1 | 10/2008 | Zemlok et al. |
| 2008/0308603 A1 | 12/2008 | Shelton et al. |
| 2009/0090764 A1 | 4/2009 | Viola et al. |
| 2009/0112229 A1 | 4/2009 | Omori et al. |
| 2009/0138006 A1 | 5/2009 | Bales et al. |
| 2010/0016853 A1 | 1/2010 | Burbank |
| 2010/0076474 A1 | 3/2010 | Yates et al. |
| 2011/0060346 A1 | 3/2011 | Jensen et al. |
| 2011/0118754 A1 | 5/2011 | Dachs, II et al. |
| 2011/0208090 A1 | 8/2011 | Parihar |
| 2013/0214029 A1 | 8/2013 | Scirica |
| 2014/0001234 A1* | 1/2014 | Shelton, IV ........... A61B 34/37 227/176.1 |
| 2016/0100838 A1 | 4/2016 | Beaupré et al. |
| 2016/0174984 A1 | 6/2016 | Smith et al. |
| 2016/0220369 A1 | 8/2016 | Chalekian et al. |
| 2018/0073615 A1 | 3/2018 | Wixey |
| 2018/0274601 A1 | 9/2018 | Saito et al. |
| 2019/0200983 A1 | 7/2019 | Wixey et al. |
| 2020/0253671 A1* | 8/2020 | Bailey .................... A61B 17/29 |

OTHER PUBLICATIONS

International Search Report and Written Opinion for Application No. PCT/US2017/050731, dated Dec. 15, 2017, 14 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

U.S. Appl. No. 16/333,924, filed Mar. 15, 2019, Medical Device Drive System.

U.S. Appl. No. 15/699,441 U.S. Pat. No. 10,591,032, filed Sep. 8, 2017, Split Nut Drive.

* cited by examiner

MEDICAL DEVICE DRIVE SYSTEM

RELATED APPLICATION

This application is a U.S. National Stage Filing under 35 U.S.C. 371 from International Application No. PCT/US2017/050731, filed on Sep. 8, 2017, and published as WO 2018/052810 A1 on Mar. 22, 2018, which claims the benefit of priority of U.S. Provisional Application 62/395,364, filed Sep. 15, 2016, each of which is herein incorporated by reference in its entirety.

BACKGROUND

Medical device systems can include components that are driven by drive mechanisms such as electric motors. Drive components such as gears, levers, and tubes can be used to translate movement through a drive system to a surgical tool. For example, surgical systems can include tools that are controlled and driven by mechanical drive systems. Surgical systems can include tools such as cutters, staplers, and cautery tools.

SUMMARY

An example medical device system can include a surgical tool, a drive system operatively coupled to the surgical tool, and a one-way input device operatively coupled to the drive system. The drive system can be drivable in a first direction to effectuate a first operation of the surgical tool, and drivable in a second direction to effectuate a second the operation of the surgical tool. The one-way input device can be operable to drive the drive system in the second direction but not the first direction. In an example, the one-way input device can include a ratchet device coupled to the drive system.

In an example, the drive system can be a rotary drive system that can include a drive gear operably coupled to a drive train that is operatively coupled to the surgical tool, and the one-way input device can include a first input gear that is operatively coupled to the drive gear. The one-way input device can include a manual input device operatively coupled to the first input gear with a ratchet mechanism.

In an example, the first input gear can include a first side, a second side, and a circumferential gear portion connecting the first and second side. The circumferential gear portion can include a plurality of gear teeth that are operatively engaged with the drive gear. The first side of the first input gear can include a first set of ratchet teeth, the one-way input device further can include a rotatable component that is rotatably coupled to the first input gear, the rotatable component can include a second set of ratchet teeth sized and shaped to engage with the first set of ratchet teeth when the rotatable component is rotated in a drive direction, the second set of ratchet teeth can be sized and shaped to move past the first set of ratchet teeth without engaging the first set of ratchet teeth when the rotatable component is rotated in a non-drive direction, wherein rotation of the rotatable component in the drive direction turns the first input gear and rotates the drive gear, and rotation of the rotation component in the non-drive direction does not drive the first input gear and drive gear. A telerobotic surgical system operatively coupled to the drive gear. The drive gear can include a first set of teeth a first engaged with the first input gear, and a second set of teeth engaged with a second input gear that is coupled to the telerobotic surgical system.

In an example, the medical device system can further include a drive support. The drive gear and drive train can be coupled to the drive support. The drive train can include a lead screw having a proximal portion coupled to the drive gear, a threaded portion, and a lead screw body extending from the proximal portion to the threaded portion, the lead screw body defining an axis. The drive train can further include a nut coupled to the threaded portion of the lead screw. The nut can be rotationally fixed relative to the drive support and axially movable relative to the drive support. The drive train can further include a drive tube coupled to the nut. The surgical tool can be coupled to the drive tube.

In an example, the medical device system can include a torque limiter configured to prevent over-torquing the drive system in the second direction. For example, the torque limiter can prevent over-torquing when a component has reached the limits of its range of motion.

In an example, actuation of the drive system in the first direction advances the surgical tool, and actuation of the drive system in the second direction retracts the surgical tool.

In an example, actuation of the drive system in the first direction closes the surgical tool, and actuation of the drive system in the second direction opens the surgical tool.

In an example, the drive system is configured to advance and retract the surgical tool along an axis, and the medical device system further includes a roll drive system configured to turn the surgical tool about the axis. In an example, the medical device system includes a roll lock system configured to selectively prevent rotation of the surgical tool about the axis, the roll lock system having a first state in which the surgical tool can be rotated about the axis, and a second state in which the surgical tool cannot be rotated about the axis.

In an example, the roll drive system can include a roll gear coupled to a roll drive train, and the roll lock system can include a first locking member and a second locking member. In the first state, the first locking member and second locking member are in an unlocked position in which the first locking member and second locking member are not engaged with the roll gear. In the second state, the first locking member and second locking member each can be in a locked position in which the first locking member and second locking member are engaged with the roll gear to prevent the roll drive system from turning the surgical tool.

In an example, the roll lock system can include a roll lock input between the first locking member and the second locking member. The roll lock input can be actuatable to move the first locking member and second locking member away from the roll drive system to disengage the first locking member and second locking member from the roll gear. The roll lock input can include a cam having a first cam surface and a second cam surface, the roll lock input can be sized and shaped such that when the roll lock input is rotated to an unlock position, the first cam surface engages the first locking member to bias the first locking member away from the roll gear, and the second cam surface engages the second locking member to bias the second locking member away from the roll gear.

An example a surgical device drive system can include a drive gear coupled to a drive train configured to interact with a surgical tool, a system input gear coupled to the drive gear, a control system coupled to the system input gear, and a manual input device. The manual input device can include a manual input component, a manual input gear, and a ratchet mechanism. The manual input gear can be coupled to the manual input component by the ratchet mechanism, and the manual input gear can be operatively coupled to the drive gear. The drive train can be operable in a first direction and a second direction. In an example, the control system can be operable to drive the drive gear and drive train in the first direction and the second direction using the system input gear, and the manual input device can be operable to drive the drive gear and drive train in the second direction, but not the first direction, using the manual input gear.

In an example, the drive gear can include a first gear element engaged with the system input gear and a second gear element engaged with the manual input gear. The surgical device drive system can be coupled to a surgical tool, and the drive train can be configured to displace the surgical tool along an axis. The surgical device drive system can further include a roll drive system configured to rotate the surgical tool around the axis. The roll drive system can include a roll gear, a roll input gear operatively coupled to the roll gear, and a roll lock component configured to engage the roll gear or roll input gear to prevent rotation of the roll gear and roll input gear.

In an example, the roll lock component can include a first roll lock arm sized and shaped to engage a tooth of the roll input gear. The roll drive system can further include a second roll lock arm sized and shaped to engage a second tooth of the roll input gear, and a roll lock input sized and shaped to engage the first roll lock arm and second roll lock arm. The first roll lock arm and second roll lock arm can be displaceable away from the roll input gear by the roll lock input to unlock the roll input gear and permit rotation of the surgical tool.

Each of these non-limiting examples can stand on its own, or can be combined in various permutations or combinations with one or more of the other examples.

This Summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Medical device drive systems can be used to control an instrument that is coupled to a drive system with a shaft. A teleoperated surgical system, for example, can employ a medical device drive system to control a surgical instrument that can be inserted into a patient to perform a surgical procedure.

Manipulation of a surgical instrument during a teleoperated surgical procedure can be difficult, due to factors such as space constraints, the size of components, the need for precision and accuracy during surgery, and the presence of multiple tools in the body. Surgical instruments can be controlled by a telerobotic control system (e.g. a portion of an Intuitive Surgical da Vinci® surgical system) that can use a combination of mechanical elements such as gears and cables to control surgical tools. It can also be desirable to manually control a surgical tool.

In an example medical system, a manual input device can be provided to allow manual operation of a tool at a proximal end of a medical device drive system. The manual input device can, for example, be integrated into a proximal portion of a drive system.

In some situations, the manual input device can be unidirectional. For example, the manual input device can be configured to retract a surgical tool, but not advance the surgical tool. In some examples, this can be accomplished using a ratchet: A manual input device can include a ratchet that actuates a drive system when the ratchet is operated in a first direction, but does not actuate the drive system when the ratchet is operated in the second direction. In some examples, the ratchet can be a rotary ratchet mechanism that is configured to turn a gear.

It can also be desirable to lock an operation of a medical device system. For example, a degree of freedom of movement or operation of a tool can be locked to maintain a surgical tool in a particular configuration or range of motion. In an example, a lock arm can be selectively engageable with a gear tooth or other actuator to lock an operation or movement of the surgical tool.

Figure 1A:
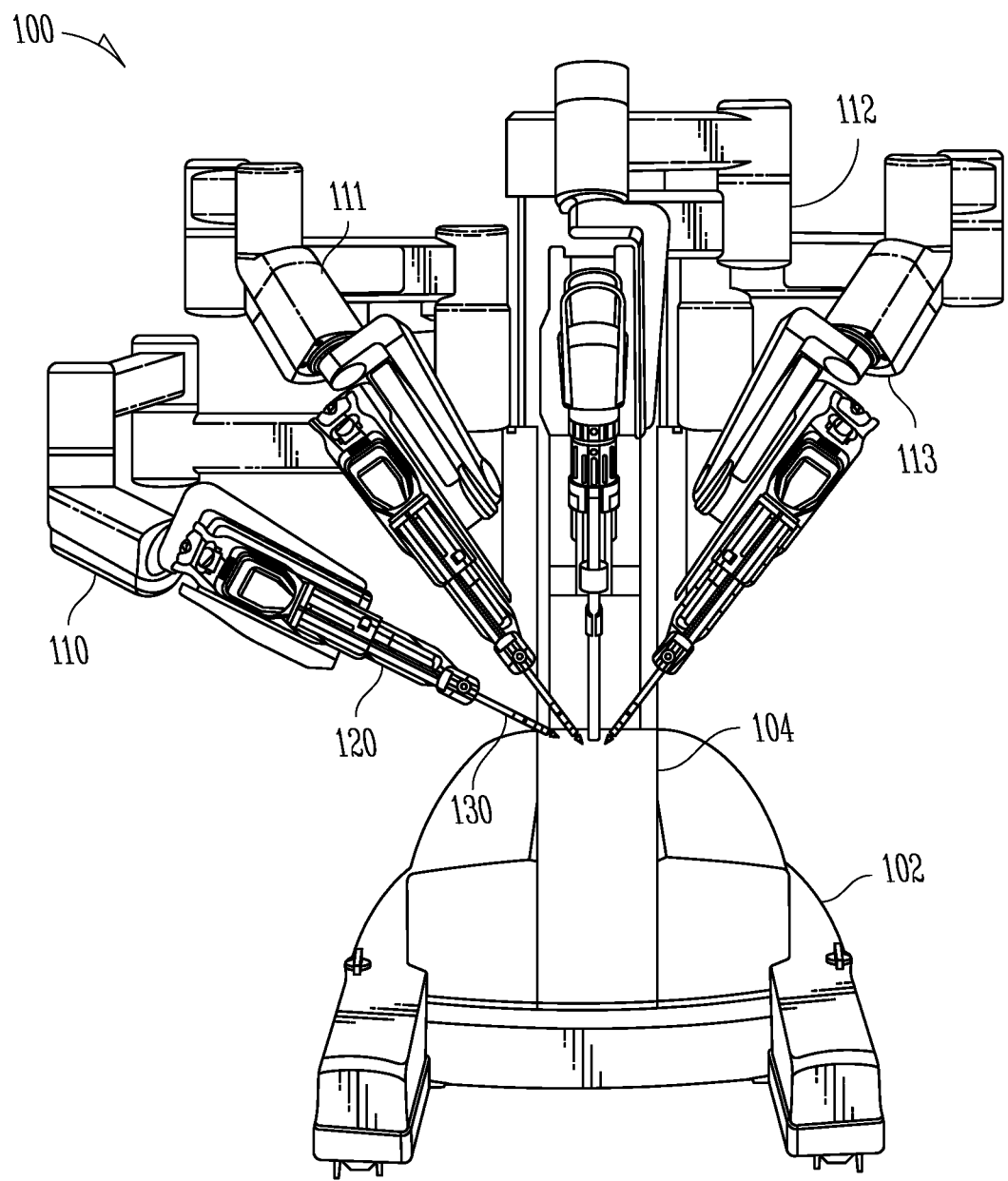
FIG. 1A is an illustration of an example instrument system for use in robot-assisted minimally invasive surgery.
Figure 1B:
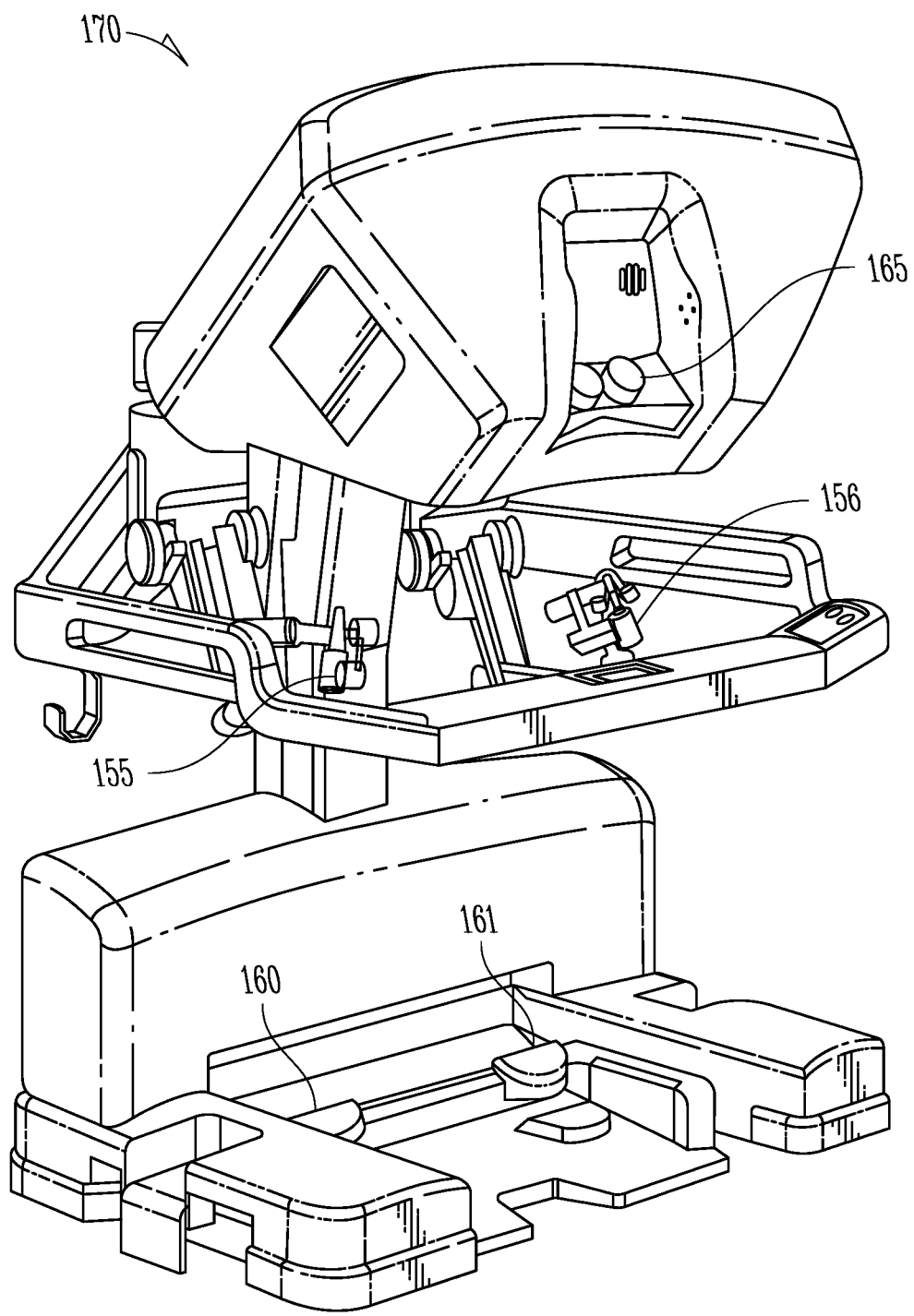
FIG. 1B is an illustration of an example physician console for use in robot-assisted minimally invasive surgery.
Figure 1C:
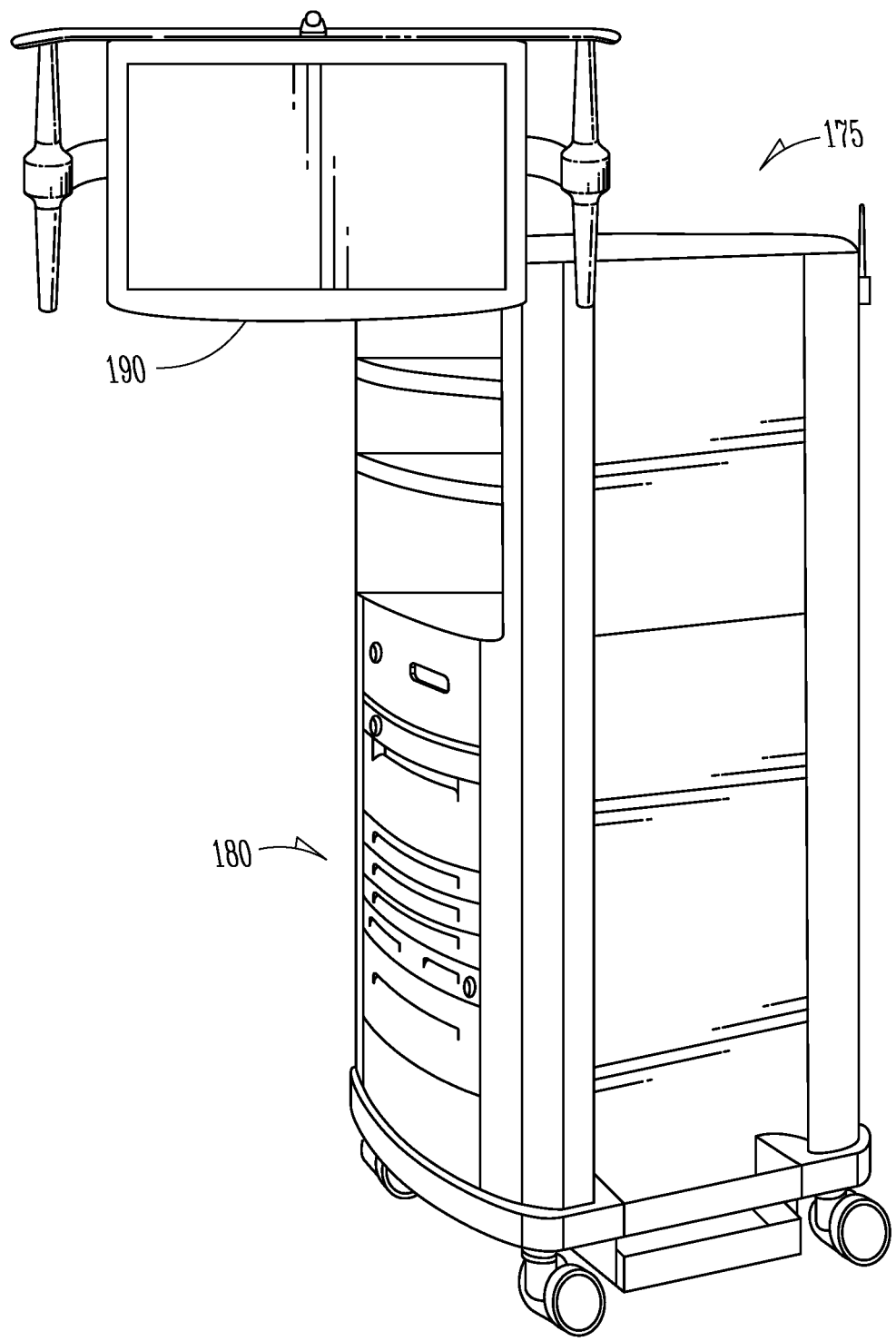
FIG. 1C is an illustration of an example control cart for use in robot-assisted minimally invasive surgery.

FIGS. 1A, 1B, and 1C illustrate an example robot-assisted minimally invasive surgical system. FIG. 1A shows an instrument system 100 (sometimes known as a "patient side cart") that can be situated near a patient operating table (not shown). FIG. 1B shows a surgeon console 170 that can include controls and a viewing system. FIG. 1C shows a control cart 175 that can include, for example, processing equipment and communication equipment.

Referring again to FIG. 1A, the system 100 can include a base 102, a support tower 104, and one or more manipulator arms 110, 111, 112, 113, which can be mounted on the support tower. Alternatively, the manipulator arms 110, 111, 112, 113 can be connected to a main boom (not shown), which can be movable. An instrument 130 can be mounted to an instrument mount 120 on one of the manipulator arms. A cannula (not shown in FIG. 1A) can be mounted to a cannula mount. An instrument 130 can be inserted through a cannula seal in the cannula, and into the patient (not shown) for use in a surgical or other medical procedure. Through movement of the manipulator arms, the orientation of the instrument can be controlled in multiple dimensions, e.g. lateral, horizontal, vertical, angular movements in one, two, or three planes.

FIG. 1B shows an example physician console 170. The physician console can include hand control 155, 156 and pedal controls 160, 161. The hand controls 155, 156, and pedal controls 160, 161 can be used to control equipment at the patient side cart. For example, portions of a distal end of an instrument can be manipulated using instrument controls. The controls can include haptic feedback features so that a physician can interpret physical information, such as resistance or vibration, through the controls. The physician console 170 can also include a viewing system 165 that can display video or other images of a surgical site.

FIG. 1C shows an example control cart 175. The control cart can include processing equipment 180 for processing controls, facilitating communication between the physician console and the patient side cart, or a remote site. The control cart 175 can also include a display 190, which can show images that the physician is seeing on the physician console, a video feed from a camera in the patient, or other information. In an example configuration, signals input at a surgeon console 170 can be transmitted to the equipment 180 on the control cart, which can interpret the inputs and generate commands that are transmitted to the patient side cart 100 to cause manipulation of an instrument 130 or portions of a manipulator arm 110. The equipment 180 is shown on a cart for exemplary purposes, but could also be arranged in various configurations, e.g., it could be integrated as part of the physician console, the patient side cart, or both, or divided between the physician console and patient side cart. The equipment can also be provided as software, hardware, or both, on an installed or remote system.

Figure 1D:
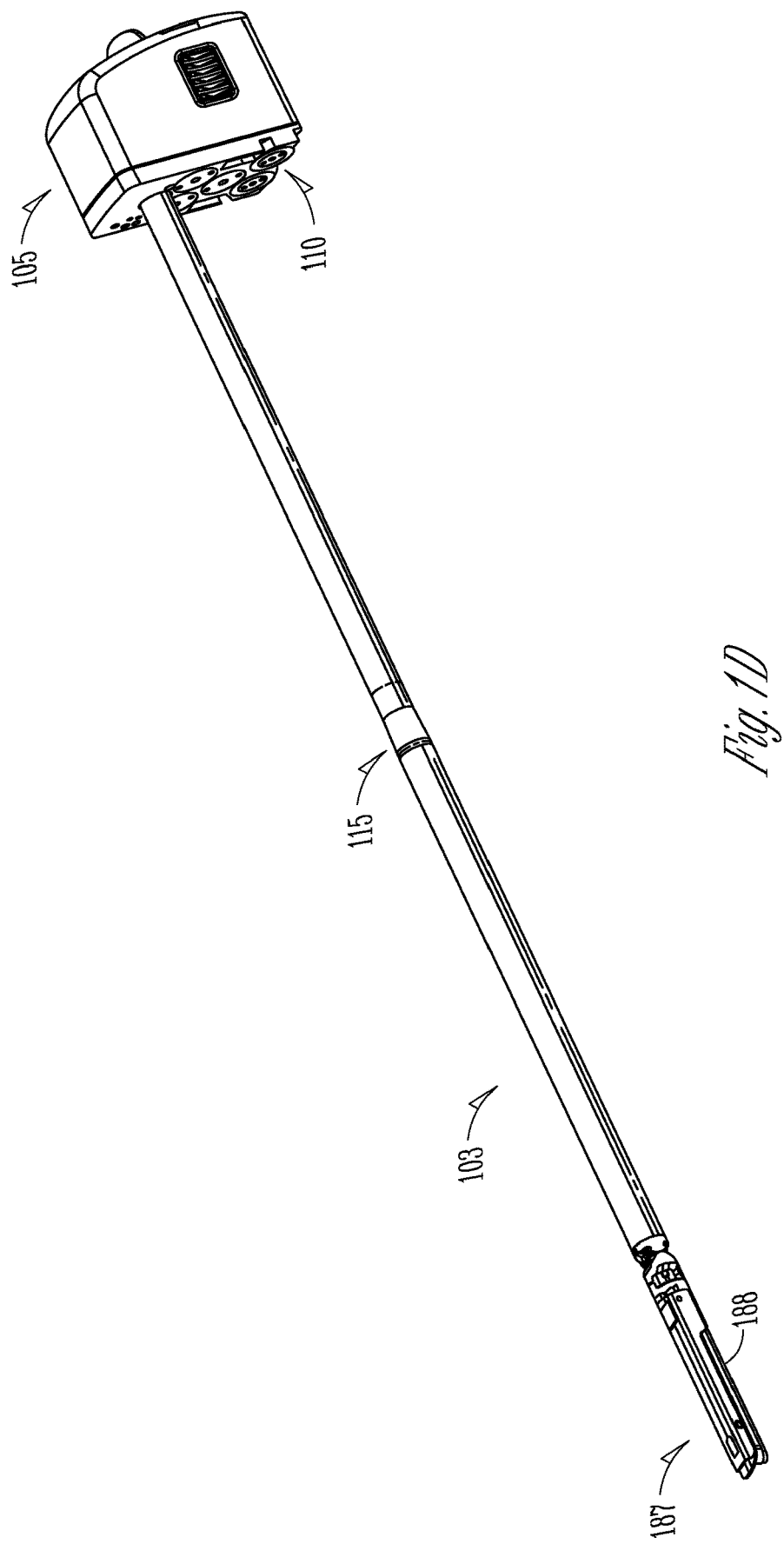
FIG. 1D is a perspective view of an example medical device drive system connected to an example surgical tool.

FIG. 1D shows an example medical device system 103 that can be mounted on and used with the instrument system 100 shown in FIG. 1A. The medical device system 103 can include a proximal portion 105 including an interface 110 that can couple to a computerized control system such as the system illustrated in FIGS. 1A, 1B, and 1C, a middle portion 115 that can include drive components such as a drive member (not shown in FIG. 1D), and a distal portion 187 that can include an surgical tool 188. The surgical tool 188 can, for example, be any of a variety of surgical tools, such as a cutter, grasper, a cautery tool, a camera, a light, or a surgical stapler. The surgical tool 188 can be the instrument 130 shown in FIG. 1A. For the purpose of this document, the terms "tool" and "instrument" are interchangeable.

Figure 1E:
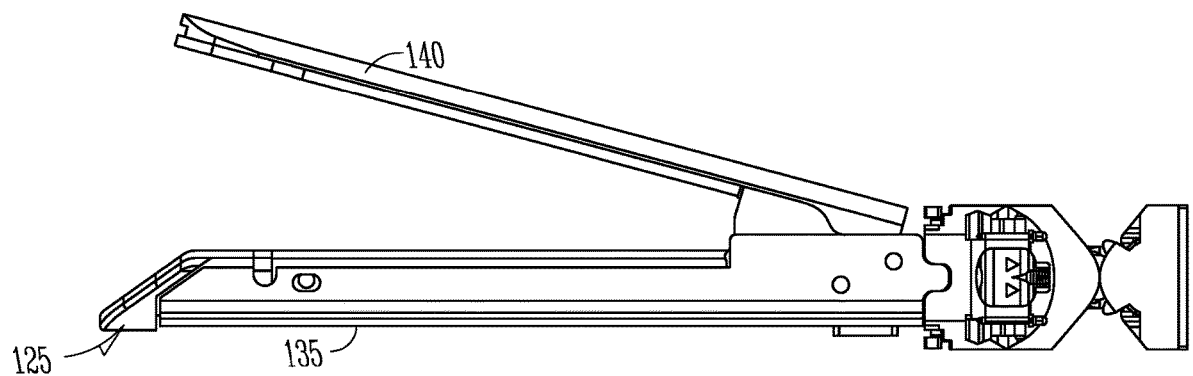
FIG. 1E is an illustration of an example surgical stapler.

FIG. 1E shows an example surgical stapler 125 that can include a lower jaw 135 and an upper jaw 140. The upper jaw 140 can close onto the lower jaw 135, at which point a series of staples can be delivered to tissue trapped between the jaws.

Figure 1F:
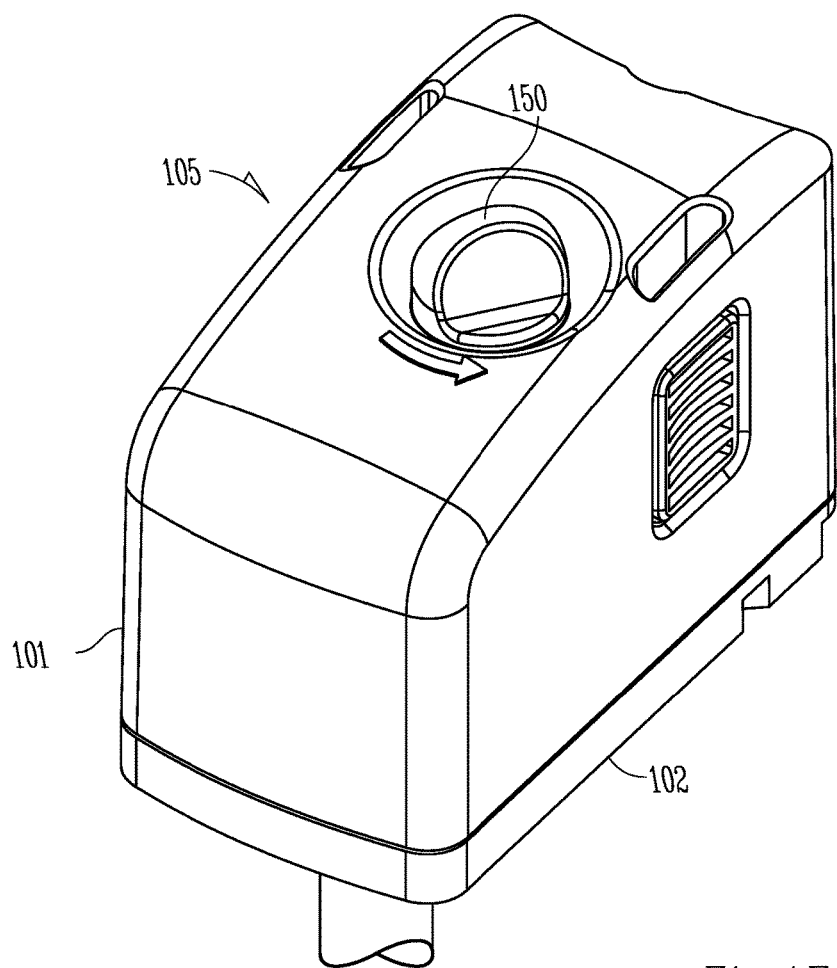
FIG. 1F is a top perspective view of the proximal portion of the medical device system.

FIG. 1F is a top perspective view of the proximal portion of the medical device system that shows a manual input device 150 and a proximal portion 105 of a medical device system 103.

Figure 2A:
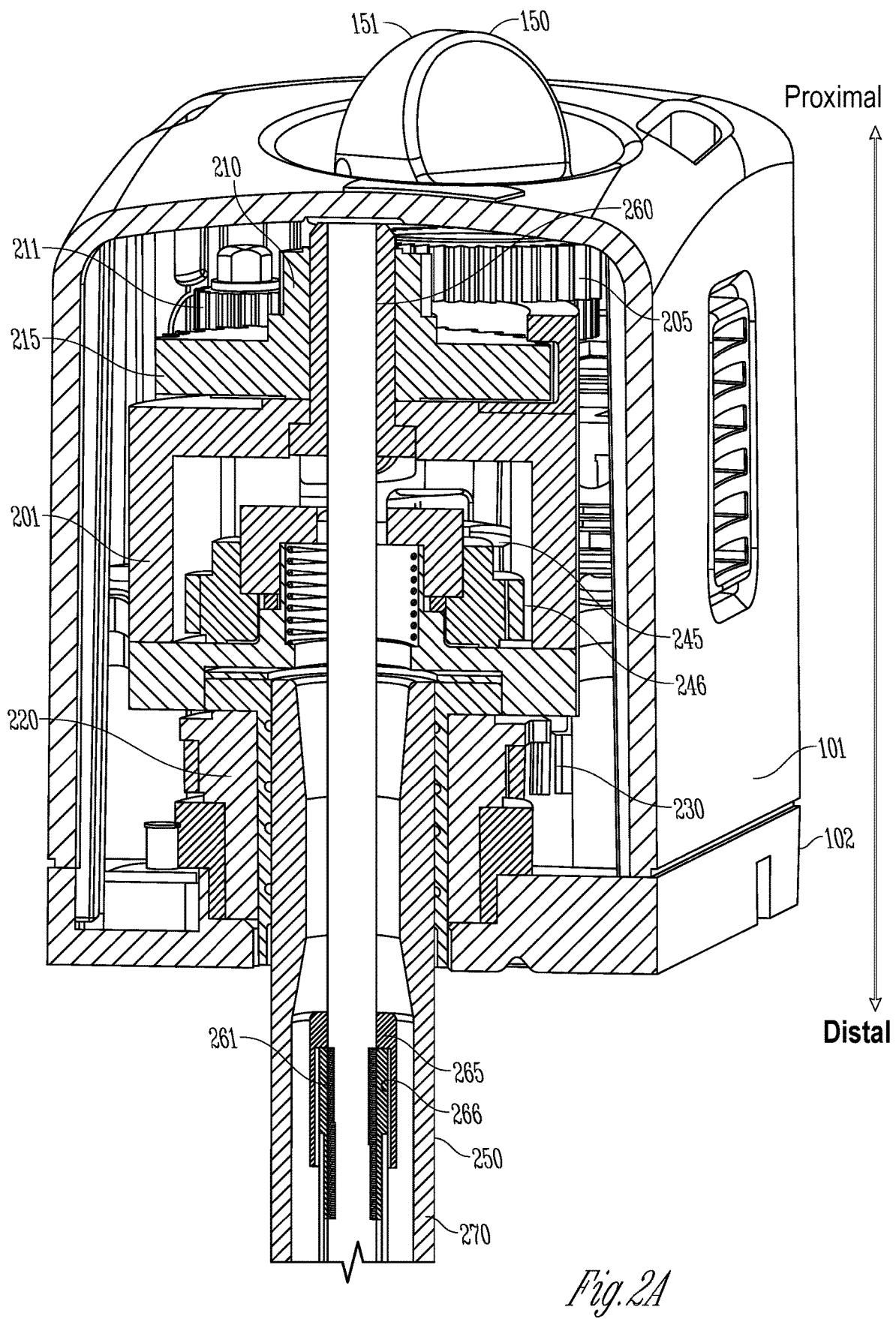
FIG. 2A is a perspective cross-sectional view of the proximal portion of the medical device system.
Figure 2B:
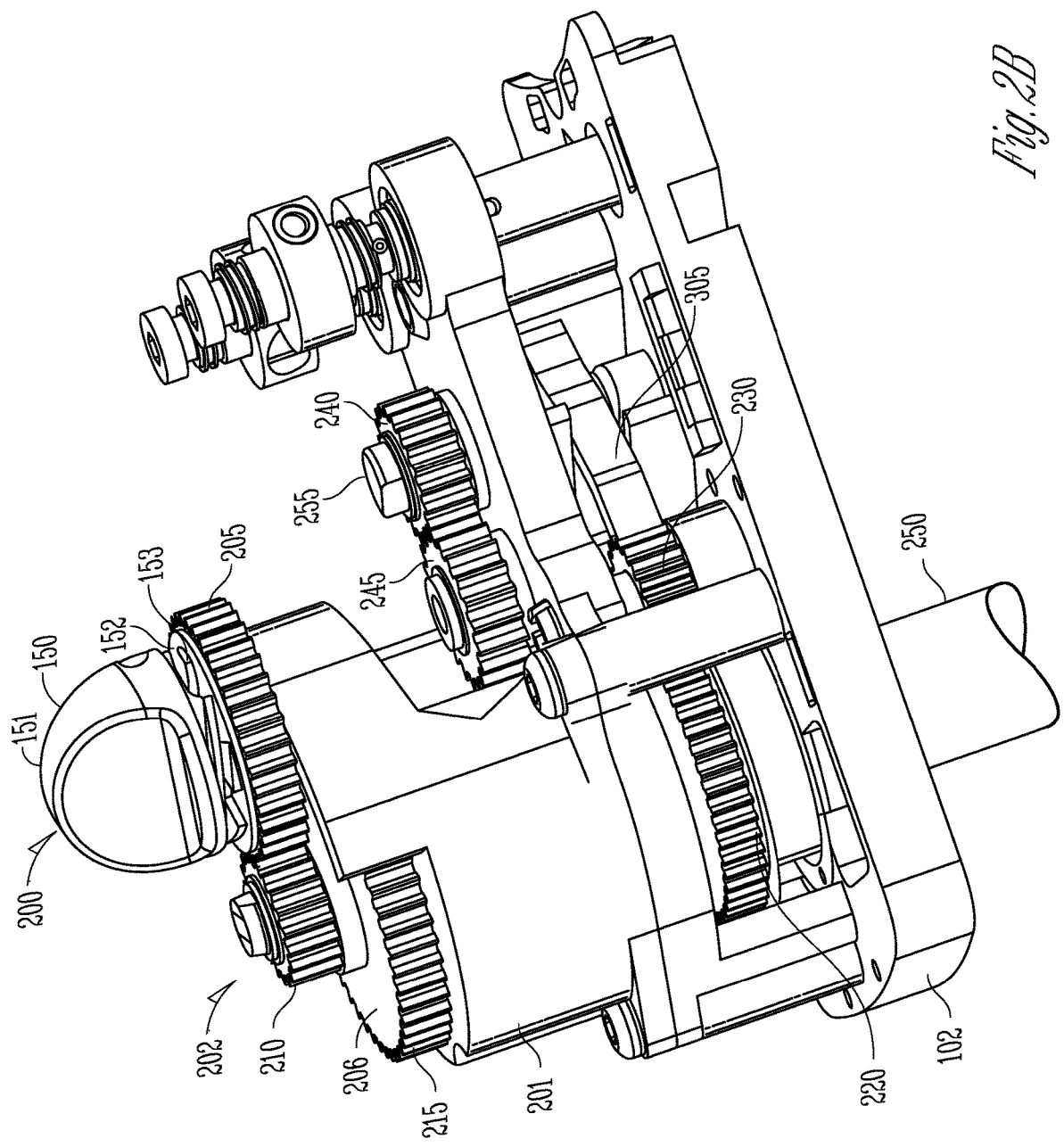
FIG. 2B is a perspective view of the proximal portion of the drive system for the medical device system shown in FIG. 2A.

FIG. 2A is a perspective cross-sectional view of the proximal portion 200 of the medical device system 103. FIG. 2B is a perspective view of a proximal portion 200 of the drive system for the medical device system 103. The components shown in FIG. 2B can be housed within the cover 101 shown in 2A.

The manual input device 150, which can, for example, include a thumb wheel, can be operatively coupled to a drive system 202 that can be coupled to a frame 201 that can include or be coupled to the mounting plate 102. The drive system 202 can, for example, include a drive train that is operatively coupled to a surgical tool. The drive system can, for example, be a rotary drive system that include a plurality of gears that can impart rotary motion on a tool, or the rotary motion can be translated to axial motion, or the rotary motion can be converted to actuation of a tool, such as opening or closing features of the tool. In an example, operation of the drive train in a first direction (e.g., clockwise) causes a first operation of a tool, and operation of the drive train in a second direction, which can be opposite the first direction (e.g., counter-clockwise) can cause a second operation of the tool. In an example, operation of the drive train in the first direction advances the tool, and operation of the drive train in the second directions retracts the tool.

As shown in FIGS. 2A and 2B, in an example, the manual input device 150 can include a graspable portion 151 such as a thumb wheel or knob that can be operatively coupled to a manual input gear 205 that can be coupled to the drive train. The manual input device 150 can, for example, be a one-way input device. In an example, that the manual input device can cause the second operation of the tool (e.g., retraction) but not the first operation of the tool (e.g., advancement).

In an example, the manual input device 150 can include a ratchet mechanism. For example, a first set of ratchet teeth 152 can be coupled to the graspable portion 151, and a second set of ratchet teeth 153 can be coupled to the manual input gear. In an example, the first set of ratchet teeth 152 are on the bottom of the graspable portion, and the second set of ratchet teeth are on a top side of the manual input gear 205. In an example, the drive system can include a torque limiter that is configured to prevent over-torquing of the drive system. The torque limiter can, for example, be incorporated into the proximal portion of the medical device system. In an example, the torque limiter can be incorporated into the manual input device 150.

Referring again to FIGS. 2A and 2B, the manual input gear 205 can be operatively coupled to a first set of teeth 210 on a first drive gear 206. The first drive gear 206 can also include a second set of teeth 215 that can be coupled to a second input gear 211, which can, for example, be coupled to a telerobotic surgical system (not shown.) The telerobotic surgical system can, for example, be the da Vinci® surgical system available from Intuitive Surgical®. In various examples, the first drive gear 206 can be a gear with multiple sets of teeth to enable operative coupling to both the manual input gear and the second input gear 211, or the first drive gear 206 can be two gears that are connected together, for example by a bolt, weld, or adhesive.

In an example, the first drive gear 206 can be driven by both the manual input gear 205 and the second input gear 211 to allow both manual control (through the manual input gear 205) and telerobotic control via a control system coupled to the second input gear 211.

As shown in FIG. 2A, the first drive gear 206 can be coupled to a lead screw 260 that is rotatably coupled to the frame 201. The lead screw can include an interface portion 261 that can engage with an interface portion 266 on a drive member 265. In an example, the drive member can be prevented from rotation, so that rotation of the lead screw 260 can drive the threaded interface portion 266 and advance the drive member 265 distally. The drive member can, for example, include a nut. The drive member 265 can be coupled to the surgical tool 188 to impart an operation or movement on the surgical tool, such as advancement of the surgical tool. In an example, the drive member 265 can include a nut coupled to a drive tube that is coupled to the surgical tool 188. In an example, the lead screw 260 can also be coupled to the surgical tool, to impart a second operation or movement on the surgical tool, such closing jaws on a stapler, delivering staples, or both.

In an example, the first set of teeth and second set of teeth can be coupled in a "free wheel" arrangement, where the first set of teeth 210 can cause rotation of the lead screw 260, the second set of teeth 215 can cause rotation of the lead screw, but the first set of teeth 210 does not cause rotation of the second set of teeth, and vice-versa.

The drive system can also include second drive gear 220, which can be coupled to a medical device shaft 250 and configured to rotate the shaft. The second drive gear 220 can be coupled to third input gear 230, which can be operatively coupled to a telerobotic surgical system. A control signal can be sent from the telerobotic surgical system to rotate the third input gear 230, which rotates the second drive gear 220. In an example, rotation of the shaft can cause a medical device that is coupled to the end of the medical device shaft 250 to roll (e.g., rotate the stapler shown in FIG. 1B about a longitudinal axis).

The drive system can also include additional gears 240, 245, 246 which can be operatively coupled to the surgical tool 120 and a surgical control system to perform additional operations or movements. For example, the additional gears 240, 245, 246 can be coupled to a drive member 270. In an example, the manual input gear 205 and second input gear 211 can be configured to advance or retract a tool, and the additional gears 240, 245, 246 can be configured to operate together to rotate, articulate, open, close, or roll the tool 188.

Figure 3A:
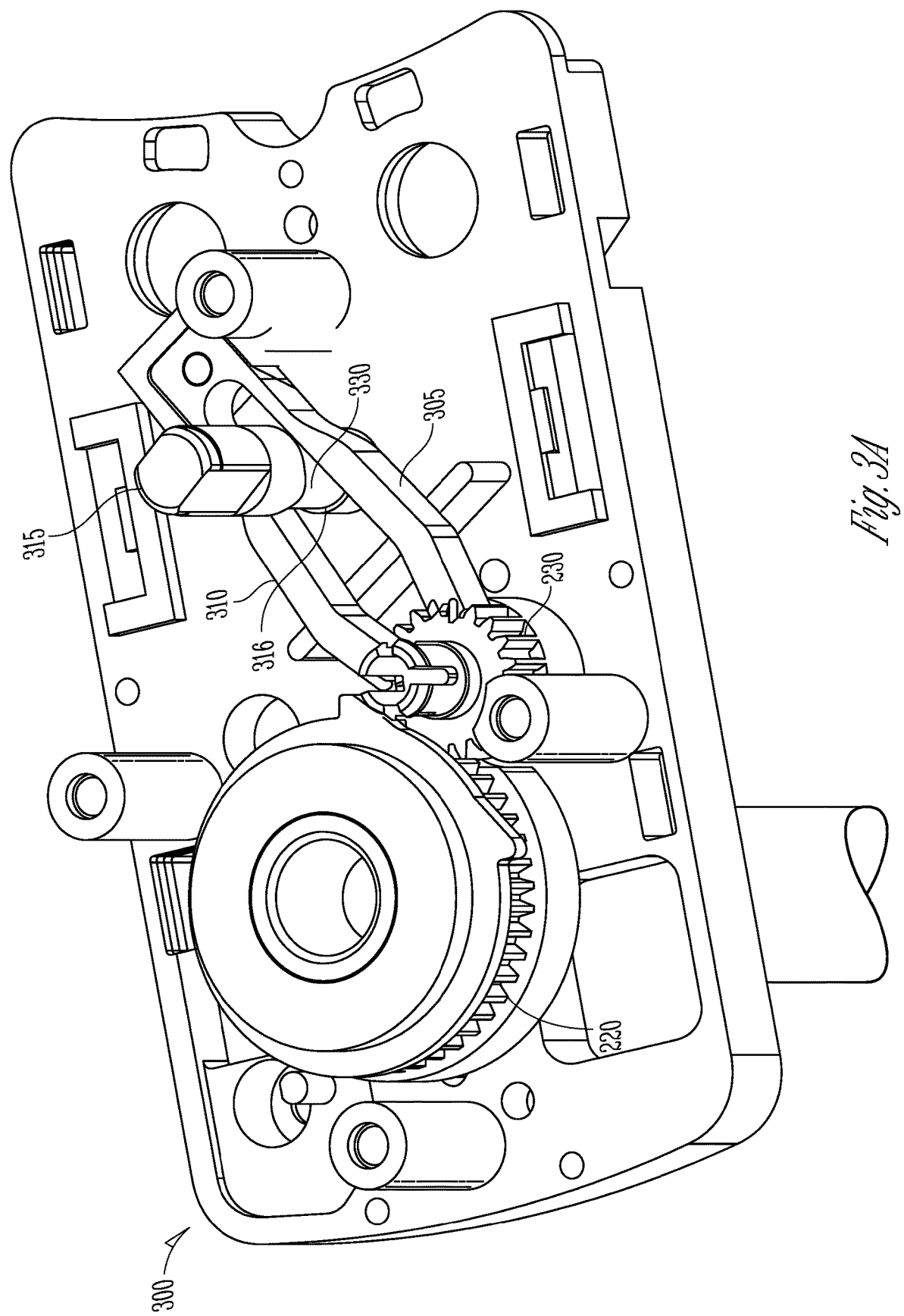
FIG. 3A is a perspective view of a roll lock system that can be incorporated into the drive system shown in FIGS. 2A and 2B.
Figure 3B:
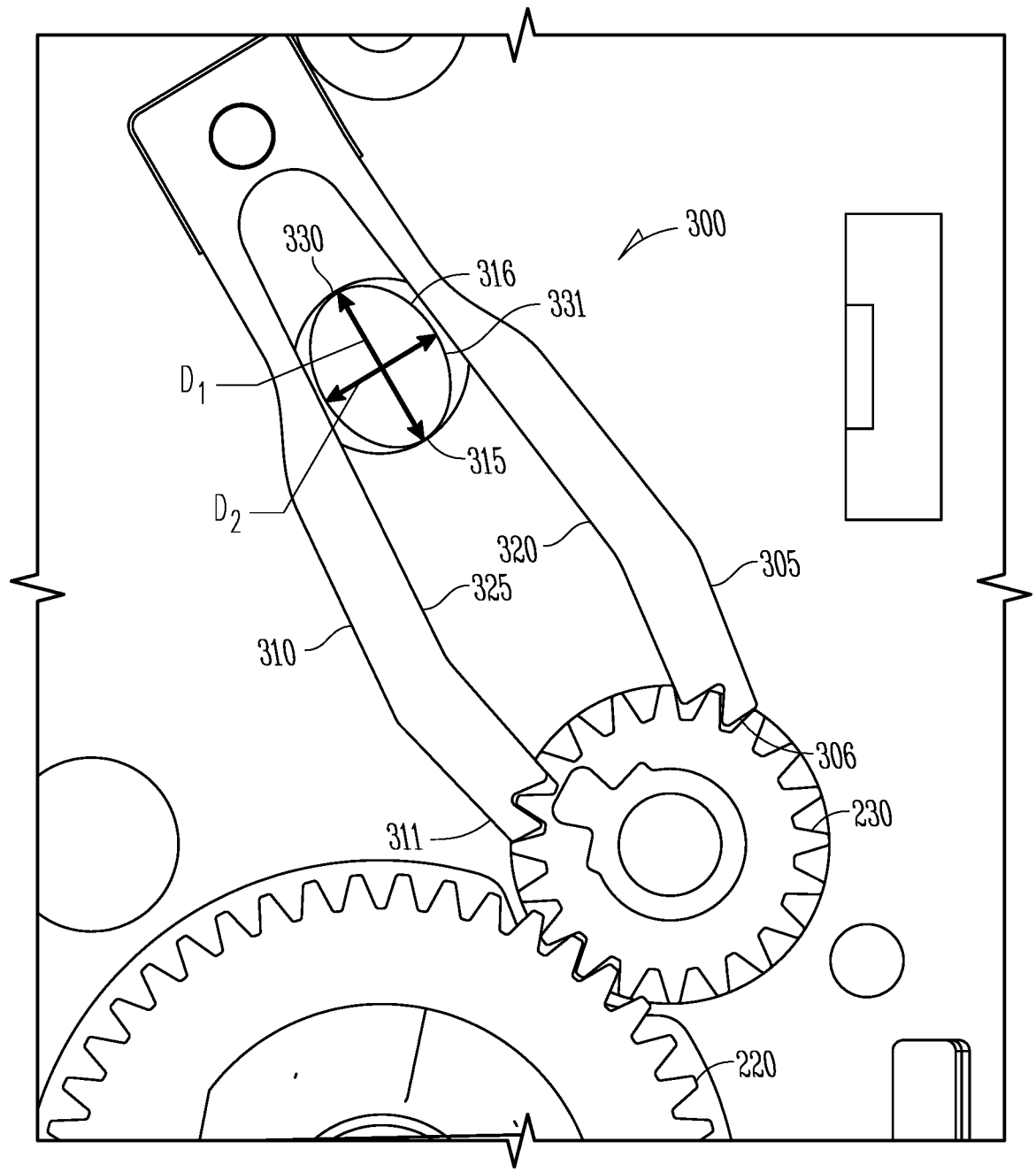
FIG. 3B is a top view of the lock system shown in FIG. 3A in a locked configuration.
Figure 3C:
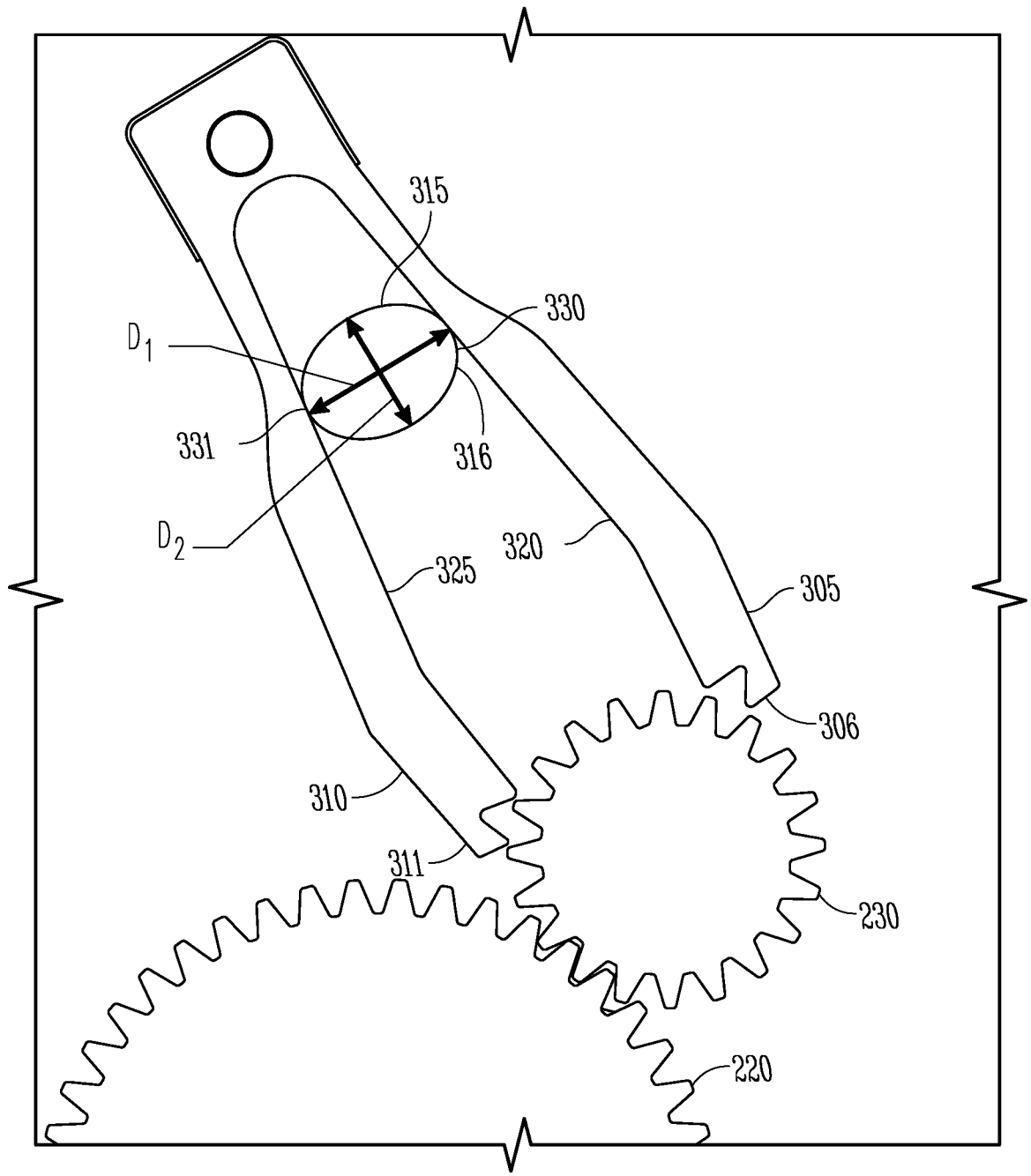
FIG. 3C is a top view of the lock system shown in FIG. 3A in an unlocked configuration.

FIG. 3A is a perspective view of an example lock system that can be incorporated into the drive system shown in FIGS. 2A and 2B. FIG. 3B is a top view of the lock system shown in FIG. 3A in a locked configuration. FIG. 3C is a top view of the lock system shown in FIG. 3A in an unlocked configuration. The lock system can be selectively opened and closed to lock and unlock an operation or movement of the surgical tool 188. As previously described, the third input gear 230 can interface with the second drive gear 220 to rotate the second drive gear 220. A locking system 300 can include a first lock arm 305 can that can include a first locking tooth 306 that can engage with the third input gear 230 to stop the rotation of the third input gear 230, and consequently "lock" the operation of the second drive gear. In an example, engaging the lock arm can lock the second drive gear 220, which prohibits an operation or movement of the surgical tool 188. For example, where drive gear 220 controls a roll operation of the surgical tool 188, engagement of the lock arm 305 and tooth 306 can prevent the drive gear 220 from turning and prevent the drive shaft 270 and surgical tool 188 from rotating, effectively "locking" the roll function of the system.

The locking system 300 can optionally include a second lock arm 310 that can include a second locking tooth 311. In an example configuration, the first lock arm 305 and second lock arm 310 can in a neutral state be engaged with the third input gear 230. A control member 315 can be configured to move the first lock arm 305 and second lock arm 310 so that the first locking tooth 306 and second locking tooth 311 are disengaged from the third input gear 230. In an example, the control member 315 can include a cam 316 that has a wide dimension $D_1$ and a narrow dimension $D_2$. The cam 316 can be situated between the first lock arm 305 and the second lock arm 310. In a first state, when the narrow dimension $D_2$ of the cam 316 extends between the first lock arm 305 and second lock arm 310, the cam 316 does not move the first lock arm 305 and second lock arm 310 out of their neutral state, or alternatively does not move the arms enough to disengage the first locking tooth 306 and second locking tooth 311 from the third input gear 230. Rotation of the cam 316 to a second state, in which the wide dimension $D_1$ extends between the arms so that a first and second outer surface 330, 331 of the cam touches inner surfaces 320, 325 of the first lock arm 305 and second lock arm 310, the cam 316 biases the arms away from each other and disengages the first locking tooth 306 and second locking tooth 311 from the third input gear. In an example, the control member 315 can be operatively coupled to a telerobotic surgical system, and a lock state of the third input gear 230 and second drive gear 220 can be controlled via controls input into a control system portion of the telerobotic surgical system.

While the locking system 300 has been described and shown for illustration purposes in conjunction with a tool roll system, the locking system can be used with any other operation to lock a selected operation.

Figure 4:
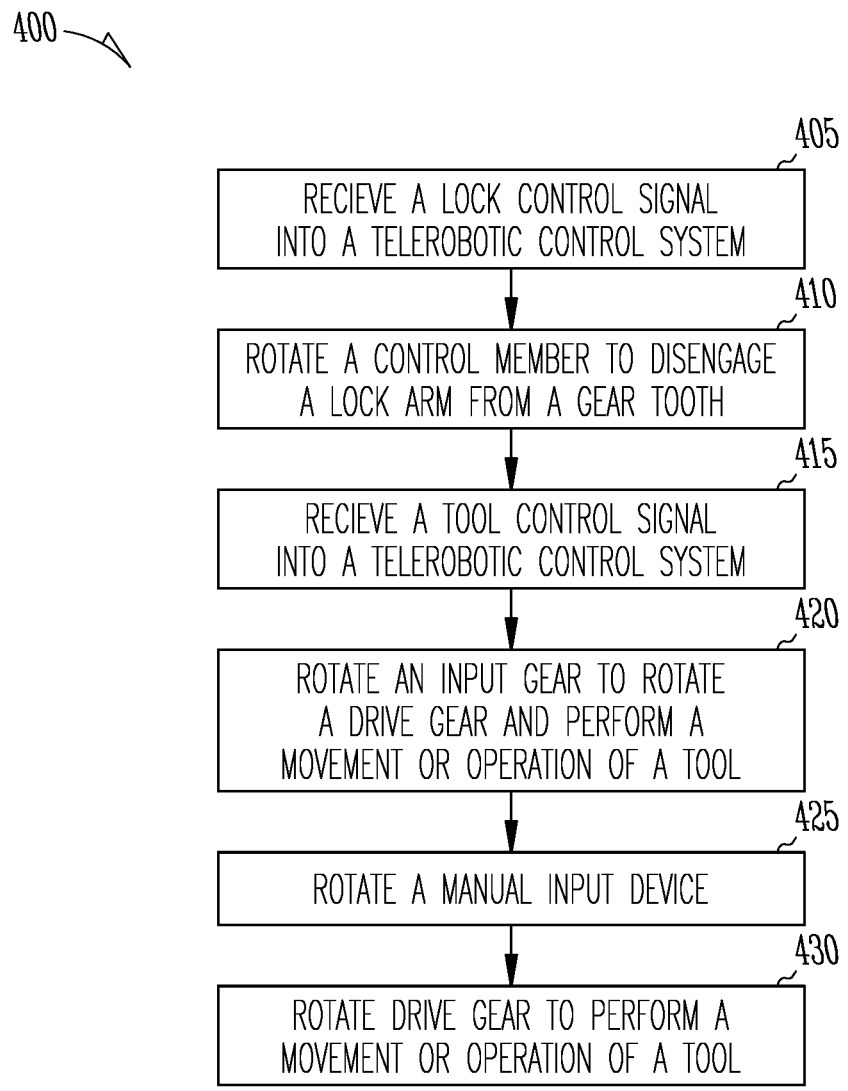
FIG. 4 is a flowchart illustration of a method of operating a lock system.

FIG. 4 is a flowchart illustration of a method 400 of operating a medical device system. The method 400 can include at step 405 receiving a control signal into a telerobotic control system. At step 410, a control member is rotated to disengage a lock arm from a gear tooth. At step 415, a control signal is sent to move an input gear. At step 420, the input gear is rotated to rotate a drive gear is rotated and perform a movement or operation of a tool that is coupled to the drive gear. The method 400 can alternatively or additionally include manually performing an operation of a tool, such as retraction of the tool. At step 425, a manual input device is rotated. At step 430, a drive gear that is coupled to the manual input device is rotated to perform a movement or operation of a tool that is coupled to the drive gear.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A medical device system comprising:
   a surgical tool;
   a drive system operatively coupled to the surgical tool, the drive system being drivable in a first direction to advance the surgical tool along an axis, and drivable in a second direction to retract the surgical tool along the axis;
   a roll drive system configured to turn the surgical tool about the axis, the roll drive system including a roll gear coupled to a roll drive train;
   a roll lock system configured to selectively prevent rotation of the surgical tool about the axis, the roll lock system including a first roll lock arm sized and shaped to engage the roll gear, a second roll lock arm sized and shaped to engage the roll gear, and a roll lock input between the first roll lock arm and the second roll lock arm, the roll lock system having a first state in which the first roll lock arm and second roll lock arm are not engaged with the roll gear, and a second state in which the first roll lock arm and second roll lock arm are each engaged with the roll gear to prevent the roll drive system from turning the surgical tool, the roll lock input being actuatable to move the first roll lock arm and second roll lock arm away from the roll drive system to disengage the first roll lock arm and second roll lock arm from the roll gear; and
   a one-way input device operatively coupled to the drive system, the one-way input device being operable to drive the drive system in the second direction but not the first direction.

2. The medical device system of claim 1, wherein the one-way input device includes a ratchet device coupled to the drive system.

3. The medical device system of claim 1, wherein the drive system is a rotary drive system that includes a drive gear operably coupled to a drive train that is operatively coupled to the surgical tool, and the one-way input device includes a first input gear that is operatively coupled to the drive gear.

4. The medical device system of claim 3, wherein the one-way input device includes a manual input device operatively coupled to the first input gear with a ratchet mechanism.

5. The medical device system of claim 3, further comprising a telerobotic surgical system operatively coupled to the drive gear.

6. The medical device system of claim 3, further comprising a drive support, the drive gear and drive train coupled to the drive support, wherein the drive train includes:
   a lead screw having a proximal portion coupled to the drive gear, a threaded portion, and a lead screw body extending from the proximal portion to the threaded portion, the lead screw body defining an axis;
   a nut coupled to the threaded portion of the lead screw, the nut being rotationally fixed relative to the drive support and axially movable relative to the drive support; and
   a drive tube coupled to the nut, the surgical tool being coupled to the drive tube.

7. The medical device system of claim 1, wherein actuation of the drive system in the first direction closes the surgical tool, and actuation of the drive system in the second direction opens the surgical tool.

8. A surgical device drive system comprising:
   a drive gear coupled to a drive train configured to interact with a surgical tool;
   a system input gear coupled to the drive gear;
   a control system coupled to the system input gear;
   a manual input device including a manual input component, a manual input gear, and a ratchet mechanism, the manual input gear being coupled to the manual input component by the ratchet mechanism, and the manual input gear being operatively coupled to the drive gear;
   wherein the drive train is operable in a first direction and a second direction, the control system being operable to drive the drive gear and drive train in the first direction and the second direction using the system input gear, and the manual input device being operable to drive the drive gear and drive train in the second direction, but not the first direction, using the manual input gear, wherein:

the drive gear includes a first gear element engaged with the system input gear and a second gear element engaged with the manual input gear;

the surgical device drive system is coupled to a surgical tool, and the drive train is configured to displace the surgical tool along an axis, the surgical device drive system further comprising a roll drive system configured to rotate the surgical tool around the axis, the roll drive system including a roll gear, a roll input gear operatively coupled to the roll gear, and a roll lock component configured to engage the roll gear or roll input gear to prevent rotation of the roll gear and roll input gear; and the roll lock component includes a first roll lock arm sized and shaped to engage a tooth of the roll input gear, the roll drive system further comprising a second roll lock arm sized and shaped to engage a second tooth of the roll input gear, and a roll lock input sized and shaped to engage the first roll lock arm and second roll lock arm, the first roll lock arm and second roll lock arm being displaceable away from the roll input gear by the roll lock input to unlock the roll input gear and permit rotation of the surgical tool.

* * * * *